(12) United States Patent
Hasegawa et al.

(10) Patent No.: US 7,863,565 B2
(45) Date of Patent: Jan. 4, 2011

(54) ELECTRON BEAM INSPECTION METHOD AND ELECTRON BEAM INSPECTION APPARATUS

(75) Inventors: Masaki Hasegawa, Sayama (JP); Hiroya Ohta, Kokubunji (JP)

(73) Assignee: Hitachi, Ltd., Tokyo (JP)

( * ) Notice: Subject to any disclaimer, the term of this patent is extended or adjusted under 35 U.S.C. 154(b) by 306 days.

(21) Appl. No.: 12/149,512

(22) Filed: May 2, 2008

(65) Prior Publication Data
US 2008/0315093 A1 Dec. 25, 2008

(30) Foreign Application Priority Data
Jun. 19, 2007 (JP) .............................. 2007-161266

(51) Int. Cl.
H01J 37/26 (2006.01)
H01J 37/29 (2006.01)

(52) U.S. Cl. ..................... 250/310; 250/306; 250/307; 250/492.1; 250/492.3; 324/500; 324/501; 324/751

(58) Field of Classification Search ................. 250/306, 250/307, 308, 310, 311, 492.1, 492.2, 492.3, 250/309; 430/296, 297, 298, 299; 324/500, 324/501, 537, 750, 751, 752, 765
See application file for complete search history.

(56) References Cited

U.S. PATENT DOCUMENTS

| | | | |
|---|---|---|---|
| 5,502,306 A | 3/1996 | Meisburger et al. | |
| 6,177,681 B1 * | 1/2001 | Nakamura | 250/559.42 |
| 6,465,781 B1 * | 10/2002 | Nishimura et al. | 250/306 |
| 6,797,954 B2 | 9/2004 | Shinada et al. | |
| 6,878,937 B1 | 4/2005 | Mankos | |
| 6,979,823 B2 | 12/2005 | Shinada et al. | |
| 7,288,948 B2 | 10/2007 | Hasegawa et al. | |
| 2003/0047682 A1 * | 3/2003 | Hatakeyama et al. | 250/310 |
| 2003/0094572 A1 * | 5/2003 | Matsui et al. | 250/310 |
| 2003/0127593 A1 * | 7/2003 | Shinada et al. | 250/310 |
| 2006/0011835 A1 | 1/2006 | Murakoshi et al. | |

(Continued)

FOREIGN PATENT DOCUMENTS

JP 05-258703 5/1992

(Continued)

Primary Examiner—Jack I Berman
Assistant Examiner—Nicole Ippolito Rausch
(74) Attorney, Agent, or Firm—Stites & Harbison, PLLC; Juan Carlos A. Marquez, Esq (57) ABSTRACT

An electron beam inspection apparatus images reflected electrons and cancels negative charging derived from electron-beam irradiation. Ultraviolet rays are irradiated and an irradiated area of ultraviolet rays is displayed as a photoelectron image. The photoelectron image and a reflected-electron image are displayed on a monitor while being superposed on each other, to easily grasp the positional relationship between the images and the difference in size between them. Specifically, the shape of the irradiated area of an electron beam includes the shape of the irradiated area of ultraviolet rays on a display screen. The intensity of the ultraviolet rays in the irradiated area of the electron beam is adjusted while the reflected-electron imaging conditions for the reflected-electron image are sustained. Moreover, an amount-of-ultraviolet ray adjustment mechanism is controlled on the monitor so that an amount of the ultraviolet rays is adjusted while observing a reflected-electron image obtained during ultraviolet irradiation.

15 Claims, 9 Drawing Sheets

U.S. PATENT DOCUMENTS

| | | |
|---|---|---|
| 2007/0085005 A1* | 4/2007 | Hasegawa et al. .......... 250/310 |
| 2007/0181808 A1 | 8/2007 | Murakoshi et al. |
| 2007/0194229 A1 | 8/2007 | Okuda et al. |
| 2007/0272857 A1 | 11/2007 | Hasegawa et al. |

FOREIGN PATENT DOCUMENTS

| | | |
|---|---|---|
| JP | 10-312765 | 5/1997 |
| JP | 11-108864 | 10/1997 |
| JP | 2002-231172 | 2/2001 |
| JP | 2006-156134 | 11/2004 |
| JP | 2006-179255 | 12/2004 |
| JP | 2005-228743 | 2/2005 |
| JP | 2006-324119 | 5/2005 |
| JP | 2007-227116 | 2/2006 |
| JP | 2007-232387 | 2/2006 |
| JP | 2007-280614 | 4/2006 |

* cited by examiner

DIRECTION OF
ULTRAVIOLET
LIGHT SOURCE

FIG.3A

RADIATION POSITION ADJUSTMENT
SCREEN IMAGE

FIG.3B

ULTRAVIOLET RADIATION INTENSITY
ADJUSTMENT SCREEN IMAGE

ULTRAVIOLET IRRADIATION POSITION
ADJUSTMENT SAMPLE

FIG.10B

ULTRAVIOLET INTENSITY
ADJUSTMENT SAMPLE

ELECTRON BEAM INSPECTION METHOD AND ELECTRON BEAM INSPECTION APPARATUS

CLAIM OF PRIORITY

The present invention claims priority from Japanese Application JP-2007-161266, filed on Jun. 19, 2007, the content of which is hereby incorporated by reference on to this application.

BACKGROUND OF THE INVENTION

1. Field of the Invention

The present invention relates to a technology for inspecting presence or absence of a foreign matter or a defect on a sample such as a wafer or a disk medium.

2. Description of the Related Art

Along with a tendency toward high-density patterning of electronic devices, the minimum line width of a patterned shape included in a large-scale integration or the size of a recording bit on a magnetic disk has been reduced down to an ultramicroscopic size of 100 nm or less. The tendencies toward the ultramicroscopic designing and high-density patterning would further continue. In the process of such high-density patterning, the presence of a small foreign matter (particles or scratches) of about 10 nm in size, which has not posed a problem previously, and a defect such as imperfect patterning causes a large defective. For example, when a pattern requested to exhibit a precision of 20 nm is formed, if a foreign matter of about 10 nm in size exists from the beginning, imperfect patterning caused by the foreign matter is of a level adversely affecting product quality. Consequently, in order to improve and sustain a product yield, the presence of such ultramicroscopic foreign matters and defects should be inspected prior to patterning, and be discriminated prior to a patterning process.

As a method of detecting such an ultramicroscopic foreign matter or defect, there is a method employing a scanning electron microscope (SEM) that sweeps a focused electron beam. For example, an SEM appearance inspection apparatus including an image processing unit that compares an acquired SEM image is employed (refer to, for example, Japanese Patent Application Laid-Open No. 05-258703). However, since the SEM appearance inspection apparatus two-dimensionally sweeps an electron beam over the surface of a sample so as to form an image, the SEM appearance inspection apparatus has a drawback that the inspection time is long. The long inspection time hinders introduction of the SEM appearance inspection apparatus into a production line in a factory for mass production of semiconductor chips or magnetic disks.

Aside from the issue of the inspection time, what impedes prevalence of an inspection apparatus employing an electron beam is an issue of charging caused by use of charged particles, that is, an electron beam. In the SEM, secondary electrons generated by an electron beam (a primary electron beam) are used to form an image. The secondary-electron generation efficiency varies depending on the energy of primary electrons or a material that emits the primary electrons. Moreover, the efficiency may exceed 1 or fall below 1. Consequently, charge applied to a specimen by primary electrons or electrons carried away by secondary electrons may be too excessive or too short. If the specimen is conducting, a significant problem will not occur. However, if the specimen is an insulator, whether charge to the specimen is too excessive or too short brings about positive or negative charging of the surface of the specimen. Charging on the surface of the specimen causes a variation in brightness of a secondary-electron image or a distortion thereof.

As mentioned above, for adaptation of an inspection apparatus that utilizes an electron beam in order to cope with the tendency toward the microscopic designing of electron devices, improvement in an inspection speed and control of charging lie as significant technological issues. In recent years, novel electron-beam applied inspection methods characteristic of a high inspection speed have been applied (refer to, for example, Japanese Patent Application Laid-Open Nos. 11-108864 and 2005-228743). The inspection technologies are such that after a negative potential close to an acceleration voltage for an electron beam to be irradiated to a sample is applied, the electron beam is irradiated to an entire inspectional field of view on the sample, and electrons reflected from the sample are focused in order to form an electron image for inspection. However, although reflected electrons are said to be focused, the technology disclosed in Japanese Patent Application Laid-Open No. 11-108864 is an inspection technology to which a mirror electron microscope (MEM) is applied so that a slightly more negative potential than an acceleration voltage for an irradiated electron beam will be applied on a sample, and electrons reflected due to the negative voltage will be imaged without colliding against the sample surface. The technology disclosed in Japanese Patent Application Laid-Open No. 2005-228743 Patent Reference 3 is an inspection technology to which a low-energy emission electron microscope (LEEM) is applied so that a more positive potential by, for example, 20 V or less than an acceleration voltage for an irradiated electron beam will be applied on a sample, the irradiated electron beam will collide against the surface of the sample with low energy, and electrons reflected from the sample surface will be imaged.

Incidentally, reflected electrons mentioned in this specification shall include both mirror electrons and low-energy emitted electrons.

On the other hand, as a control technology for charging caused by an electron beam, technologies for canceling charging that occurs during observation of an insulator sample using an SEM have been proposed (refer to, for example, Japanese Patent Application Laid-Open Nos. 10-312765 and 2002-231172). In the conventional technologies, ultraviolet rays are irradiated in order to make the insulator surface conductive so as to cause charge to flee. Otherwise, ultraviolet rays are used to generate photoelectrons so as to change the surface in a direction of positive charging, and a negatively charged insulating film is thus neutralized in order to cancel charging on the insulator surface.

SUMMARY OF THE INVENTION

In the above inspection technologies, since an irradiated electron beam approaches or collides against a sample with low energy, if the sample to be inspected is an insulator, the irradiated electron beam causes negative charging to occur on the surface of the sample. Even in reflection of an electron beam in a mirror electron microscope, the energy of an irradiated electron beam is not monoenergetic but the irradiated electron beam includes electrons of slightly higher energy. The electrons collide against the sample surface. If the sample surface is negatively charged, a reflected-electron image deteriorates. This poses a problem in that the sensitivity in detecting a defect or foreign matter is degraded.

Therefore, the charging on the surface of the insulator has to be canceled or alleviated. However, the conventional charging cancellation method employing ultraviolet rays cannot be applied for reasons described below.

First, in the conventional method, means for observing an irradiated area of ultraviolet rays, that is, a range within which positive charging occurs is unavailable. The ultraviolet irradiation area is much larger than an electron-beam irradiation area, that is, a range within which negative charging occurs. Unless the ultraviolet irradiation area is limited in the electron-beam irradiation area, extremely positive charging occurs in the outer area of electron-beam irradiation area where there are no negative charges provided.

Secondly, in the conventional method, there is no means for balancing a magnitude of negative charging, which occurs during reflection of an electron beam, and a magnitude of positive charging derived from irradiation of ultraviolet rays. Unless both the magnitudes of charging are balanced, positive or negative charging progresses. Consequently, charging is not canceled but positive or negative charging is left intact.

For the above reasons, in the conventional technology, an inspection apparatus that images reflected electrons has a drawback that charging cannot be canceled.

Accordingly, an object of the present invention is to provide an inspection technology that is implemented in an electron beam inspection apparatus which images reflected electrons, and that dissolves negative charging, which is derived from electron-beam irradiation, from a sample made of an insulating material, and detects an ultramicroscopic foreign matter or defect highly sensitively at a high speed.

In order to accomplish the above object, in the present invention, an operating mode in which photoelectrons derived from ultraviolet irradiation are imaged is additionally included so that an irradiated area of ultraviolet rays can be displayed as a photoelectron image. Moreover, the photoelectron image and a reflected-electron image are displayed on a monitor while being superposed on each other so that the positional relationship between the images and the difference between the sizes of the images can be easily grasped. In other words, the shape of an irradiated area of an electron beam includes the shape of an irradiated area of ultraviolet rays on a display screen. The intensity of ultraviolet rays in the electron-beam irradiation area is adjusted while the reflected-electron imaging conditions for a reflected-electron image are not violated.

Further, the position and size of an ultraviolet light source can be adjusted so that an irradiated area of electron-beam will include an irradiated area of ultraviolet rays, while being discerned on a monitor. Moreover, an amount-of-ultraviolet ray adjustment mechanism can be controlled on a monitor so that an amount of ultraviolet rays can be adjusted while a reflected-electron image is observed during ultraviolet ray irradiation.

Examples of configurations characteristic of the present invention will be described below.

(1) An electron beam inspection apparatus in accordance with the present invention includes: an electron optical system that irradiates an electron beam, which is emitted from an electron source, to a range covering a field of view on a sample; means for applying a voltage to the sample; an electron-beam imaging means for converging electrons, which are reflected from the sample due to the irradiated electron beam, so as to acquire a reflected-electron image; means that has the sample mounted thereon and moves the sample with respect to the irradiated electron beam; means that uses the reflected-electron image to extract a foreign matter or defect on the sample, and records the position of the foreign matter or defect or an image thereof; and an ultraviolet irradiation system that irradiates ultraviolet rays to the sample. The inspection apparatus further includes means for limiting the shape of the irradiated area of the ultraviolet rays within the shape of the irradiated area of the electron beam, and means for adjusting the intensity of the ultraviolet rays in the electron-beam irradiation area while sustaining the reflected-electron imaging conditions for the reflected-electron image.

(2) The electron beam inspection apparatus in accordance with the present invention includes means that uses the electron-beam imaging means to converge photoelectrons, which are generated from the sample due to irradiation of ultraviolet rays, so as to acquire a photoelectron image, and displays the irradiated area of the ultraviolet rays.

(3) The electron beam inspection apparatus in accordance with the present invention includes means that adjusts the position and size of the ultraviolet irradiation area so that the contour of the photoelectron image will be limited within the contour of the reflected-electron image.

(4) The ultraviolet rays and electron beam are irradiated simultaneously. The intensity of the ultraviolet rays is adjusted while the reflected-electron imaging conditions for the reflected-electron image are sustained, and negative charging that has occurred in the electron-beam irradiation area due to the irradiated electron beam is neutralized.

(5) The ultraviolet irradiation system includes an ultraviolet light source and a reflecting surface that changes the advancing direction of ultraviolet rays from one to another so that the ultraviolet rays will be irradiated to the sample.

(6) The reflecting surface is mounted in the middle of the electron optical system, and has an opening, through which the electron beam passes and which is intended to align the direction in which the electron beam is irradiated to the sample with the direction in which the ultraviolet rays are irradiated to the sample.

(7) The ultraviolet irradiation system includes means that adjusts an amount of ultraviolet rays and a pinhole between the ultraviolet light source and reflecting surface.

(8) A diaphragm for limiting a field of view is mounted on the optical path of the electron optical system. The diaphragm and pinhole are used to limit the shape and size of the irradiated area of the ultraviolet rays in those of the electron-beam irradiation area.

(9) An electron beam inspection apparatus in accordance with the present invention includes: an electron optical system that shapes an electron beam emitted from an electron source, into a planar electron beam, and irradiates the electron beam to a range covering a field of view on a sample; means for applying a negative voltage to the sample; an electron-beam imaging means that focuses electrons, which are reflected from the sample due to the irradiated electron beam, so as to acquire a reflected-electron image; means that has the sample mounted thereon and moves the sample with respect to the irradiated electron beam; means that uses the reflected-electron image to extract a foreign matter or defect on the sample, and records the position of the foreign matter or defect or an image thereof; and an ultraviolet irradiation system that irradiates ultraviolet rays to the sample. The inspection apparatus further includes: means for limiting the shape of the irradiated area of the ultraviolet rays in the shape of the irradiated area of the electron beam; and means for adjusting the intensity of the ultraviolet rays in the electron-beam irradiation area while sustaining the reflected-electron imaging conditions for the reflected-electron image. Negative charging in the electron-beam irradiation area derived from the irradiated electron beam is neutralized.

(10) Moreover, an electron beam inspection method in accordance with the present invention includes: a step of irradiating an electron beam to a range covering a field of view on a sample, to which a voltage is applied, through an electron optical system; a step of converging electrons, which are reflected from the sample due to the irradiation of the electron beam, so as to acquire a reflected-electron image; a step of using the reflected-electron image to extract a foreign matter and defect on the sample, and recording and displaying the position of the foreign matter or defect or an image thereof; and a step of alleviating negative charging on the sample, which is derived from the electron-beam irradiation, by irradiating ultraviolet rays. The inspection method further includes a step of limiting the shape of the irradiated area of the ultraviolet rays in the shape of the irradiated area of the electron beam, and a step of adjusting an amount of ultraviolet rays in the electron-beam irradiation area while sustaining the reflected-electron imaging conditions for the reflected-electron image.

According to the present invention, positive charging derived from ultraviolet irradiation and negative charging occurring during imaging of reflected electrons can be well balanced. Negative charging derived from electron-beam irradiation can be dissolved from a sample made of an insulating material, and an ultramicroscopic foreign matter or defect can be highly sensitively detected at a high speed.

DESCRIPTION OF THE PREFERRED EMBODIMENTS

Referring to the drawings, the constituent features of embodiments of the present invention will be described below.

Embodiment 1

Figure 1:
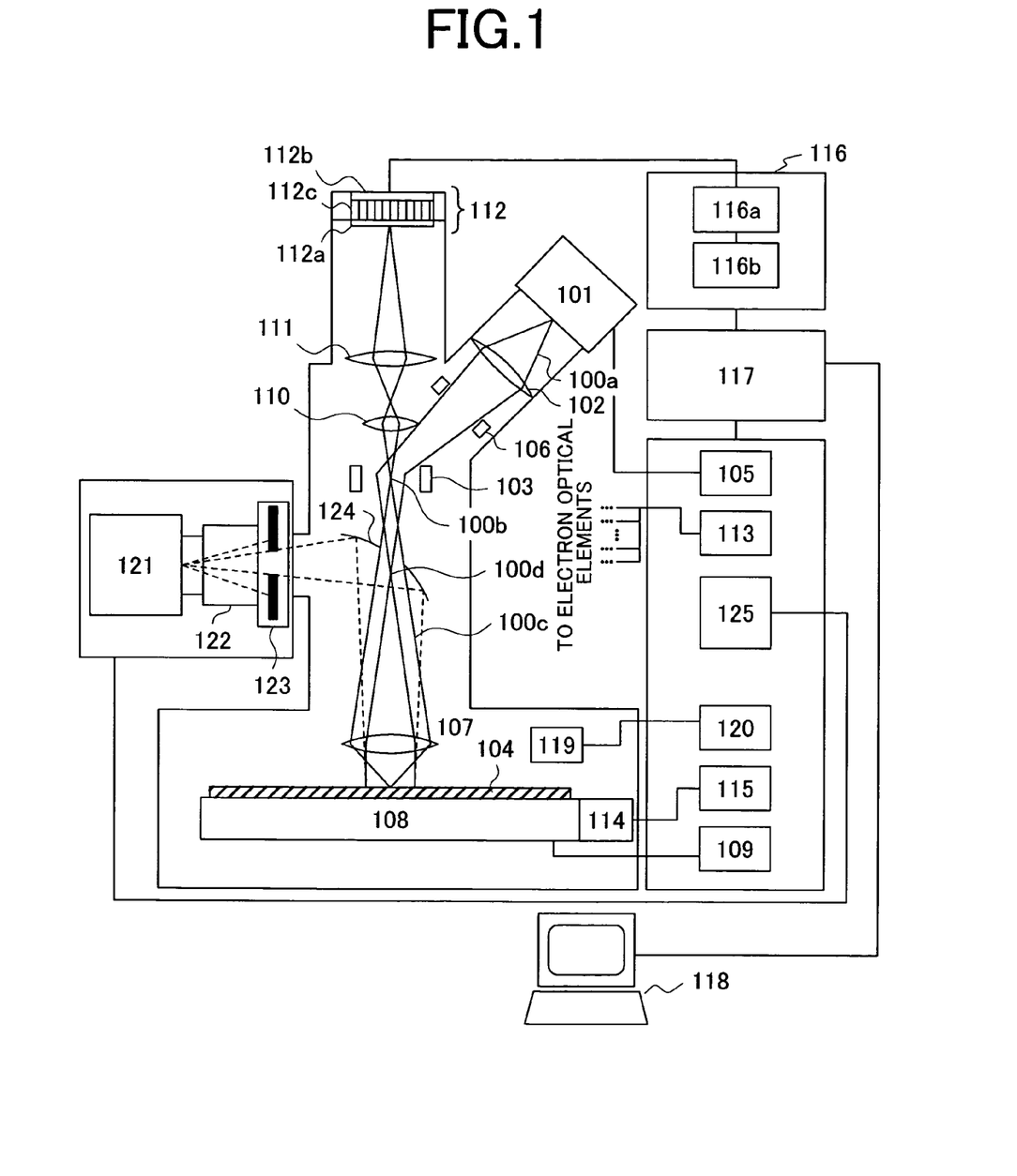
FIG. 1 is an explanatory diagram showing the fundamental configuration of an electron beam inspection apparatus that is an embodiment of the present invention.

FIG. 1 shows an embodiment of a hardware configuration of a reflected-electron imaging type electron beam inspection apparatus in which the present invention is implemented. Noted is that a vacuum exhaust pump and its control unit, and an exhaust pipe are not shown in the drawing. Moreover, for convenience' sake, the ratio of dimensions is appropriately modified.

To begin with, the major elements of an electron optical system of the present apparatus will be described below. An irradiated electron beam $10a$ emitted from an electron gun 101 is deflected by an E×B deflector 103 while being focused by a condenser lens 102. After forming a crossover $100d$, the electron beam is irradiated as a bundle of substantially parallel rays to a sample 104. In the drawing, the condenser lens 102 is drawn as one lens. Alternatively, a system having multiple electron lenses combined may be adopted in order to optimize optical conditions. As the electron gun 101, a Zr—O/W Schottky electron source is normally adopted, but an electron source made of lanthanum boride ($LaB_6$) or the like may be adopted for a large current. Voltages and currents required for running, such as, an extracting voltage to be applied to the electron gun 101, an acceleration voltage required for the electron beam, and a heating current for a filament in an electron source are fed and controlled from and by an electron gun control device 105.

The E×B deflector 103 is mounted near an imaging plane $100b$ for a focused electron beam $100c$. At this time, the irradiated electron beam $100a$ undergoes an aberration of the E×B deflector 103. If the aberration has to be compensated, another E×B deflector 106 for compensating the aberration is interposed between the irradiation system condenser lens 102 and E×B deflector 103. The irradiated electron beam $100a$ having been deflected along an axis perpendicular to the sample 104 by the E×B deflector 103 is shaped into a planar electron beam, which falls in a direction perpendicular to the surface of the sample 104, by an objective lens 107. Since a crossover is formed on the focal plane of the objective lens 107 by the irradiation system condenser lens 102, an electron beam exhibiting excellent parallelism can be irradiated to the sample 104. A field on the sample 104 to which the irradiated electron beam $100a$ is irradiated has a large area of, for example, 10000 $\mu m^2$.

A negative potential close to an acceleration voltage for an electron beam is applied on the sample 104 to be inspected that is mounted on a sample stage 108. The irradiated electron beam $10a$ is reflected from near the surface of the sample 104, and drawn upward due to the negative potential. Feed and control of a voltage to be applied to the sample 104 are performed by a sample voltage control device 109. In order to reflect irradiated electrons as closely as possible to a sample, the difference from the acceleration voltage for the irradiated electron beam $10a$ has to be highly precisely adjusted. The sample voltage control device 109 is therefore interlocked with the electron gun control device 105 for control.

Electrons reflected from near the sample undergo the focusing operation of the objective lens 107. Since the E×B deflector 103 is controlled not to exert a deflecting operation for an electron beam having advanced from below, the electrons rise perpendicularly as they are. The electrons are magnified and projected onto an image detection unit 112 by an intermediate lens 110 and a projection lens 111. In this drawing, the projection lens 111 is depicted as one lens, but may include multiple electron lenses for the purpose of attainment of a high magnification or compensation of an image distortion. The image detection unit 112 converts an image into an electric signal and transmits a reflected-electron image of the surface of the sample 104 to an image processing unit 116. Control of the electron optical system is assigned to an electron optical system control device 113.

Next, the image detection unit 112 will be described. For image detection, a fluorescent screen 112 for use in converting the reflected-electron image into an optical image and an optical image detector 112b are optically coupled together by an optical image transfer system 112c. An optical fiber bundle is adopted as the optical image transfer system 112c. The optical fiber bundle has the same number of thin optical fibers as the number of pixels bundled, and can efficiently propagate an optical image. Moreover, if a fluorescent image having a sufficient amount of light can be obtained, when an optical transfer efficiency may be low, an optical lens system may be substituted for the optical fiber bundle, and an optical image on the fluorescent screen 112a may be focused on a light receiving surface of the optical image detector 112b through the optical lens. Moreover, an amount-of-light amplifier may be inserted into the optical image transfer system 112c in order to transfer an optical image, which has a sufficient amount of light, to the optical image detector 112b. The optical image detector 112b converts the optical image focused on the light receiving surface thereof into an electric image signal, and outputs the image signal. As the optical image detector 112b, an image device supporting both a mode in which an image of a subject that normally stands still is acquired, and a mode in which an image of a time delayed integration (TDI) type of a moving object is acquired is adopted.

The image processing unit 116 includes an image signal storage block 116a and a defect decision block 116b. The image storage block 116a acquires electron optical conditions, image data, and stage position data from the electron optical system control device 113, image detection unit 112, and stage control device 115 respectively, and stores the image data in relation to a coordinate system defined on the sample. The defect decision block 116b uses the image data related to coordinates on the sample to make a decision on a foreign matter or a defect according to any of various defect decision methods such as comparison with a predetermined value, comparison with an adjacent pattern image, and comparison with an image of an identically patterned place. Coordinates representing the position of a defect are transferred to an inspection apparatus control unit 117, and stored therein. Any of the defect decision methods is designated by a user, or a method associated in advance with a kind of sample is selected by the inspection apparatus control unit 117.

Operating conditions for each component of the apparatus are inputted or outputted from or to the inspection apparatus control unit 117. Various conditions such as an acceleration voltage for generation of an electron beam, a sample stage moving velocity, and the timing of fetching an image signal from an image detection element are inputted in advance to the inspection apparatus control unit 117. The inspection apparatus control unit controls the control devices relevant to various elements on a centralized basis, and serves as an interface with a user. The inspection apparatus control unit 117 may be formed with multiple computers to which roles are assigned and which are interlinked over communication lines. Moreover, a monitor-inclusive input/output device 118 is installed.

In the present invention, retaining the difference between the surface potential of a sample and an acceleration voltage at a constant value is essential for stable detection sensitivity. For example, assuming that an inspecting operation is executed for a sample that is an insulating film, the potential on the surface of the insulating film must remain constant. If the potential on the surface of the insulating film varies during inspection, a certain voltage has to be applied in order to make the potential on the surface uniform before an inspection image is acquired. A preliminary charger 119 is therefore included. The preliminary charger 119 is controlled by a preliminary charging control device 120. The operation of the preliminary charger is defined by a known technology (refer to JP-A-2004-14485).

Next, an ultraviolet irradiation system included for neutralizing (or canceling) negative charging caused by an irradiated electron beam will be described below. The ultraviolet irradiation system includes an ultraviolet light source 121, an ultraviolet transportation system 122, a pinhole 123, and a reflecting mirror 124. The ultraviolet light source 121 generates ultraviolet rays that have energy which causes a sample to exert a photoelectric effect. The ultraviolet light source 121 may be a light source that generates, like an excimer laser that provides monochromatic light or a light source that generates light of energy falling within a certain range covering necessary energy. Even a unit including a spectroscope and a mechanism for selecting specific energy from a certain energy range shall be regarded as a light source. The ultraviolet light source 121 irradiates the pinhole 123, and the reflecting mirror 124 forms a reduced image of the pinhole 123 on the sample. Since a reduction ratio offered by the reflecting mirror 124 remains constant, the size of an irradiated area designation light source has to be adjusted in order to limit an ultraviolet irradiation area in an electron-beam irradiation area. Consequently, the pinhole 123 is realized with a light interceptive screen having pinholes of different diameters, or a device including a mechanism that can vary the diameter of a pinhole, such as, an iris diaphragm. Moreover, in order to adjust the positional relationship to the electron-beam irradiation area, the pinhole 123 is two-dimensionally movable on a plane perpendicular to an ultraviolet ray axis.

The ultraviolet transportation system 122 is included in a case where an ultraviolet intensity cannot be adjusted by the ultraviolet light source 121. As far as a beam current value remains constant, a quantity of negative charge (electrons) fed to the sample by the irradiated electron beam 100a remains constant. The ultraviolet intensity should be adjusted so that the same quantity of photoelectrons as the quantity of negative charge, which is excessively fed by the irradiated electron beam 100a, will be generated due to ultraviolet irradiation. Since the photoelectron generation efficiency varies depending on a material, an optimal amount of ultraviolet rays varies depending on a sample. Consequently, a facility for adjusting an amount of ultraviolet rays is a must. If the ultraviolet light source 121 has an intensity modulation capability, there is no problem. If the ultraviolet light source does not have the intensity modulation capability, the ultraviolet transportation system 122 is used to adjust an amount of light. As the simplest measures, the ultraviolet transportation system 122 is formed with a stretchable and contractile pipe. If the length of the ultraviolet transportation system 122 is increased, the distance between the ultraviolet light source 121 and pinhole 123 gets longer. Therefore, an amount of ultraviolet rays that passes through the pinhole decreases. In contrast, if the length of the ultraviolet transportation system 122 is decreased, the amount of light increases. If the overall length of the ultraviolet transportation system cannot be modified in terms of the configuration of the apparatus, the ultraviolet transportation system 122 is realized with a Kohler illumination optical system including an aperture stop and a lens.

Turning on or off of the ultraviolet light source 121, intensity modulation for the ultraviolet light source, ultraviolet intensity adjustment to be performed using the ultraviolet transportation system 122, and adjustment of the size or position of the pinhole 123 are controlled by the ultraviolet irradiation control device 125. The ultraviolet irradiation control device 125 performs all operations relevant to ultraviolet irradiation in response to a command sent from the inspection apparatus control device 117.

Figure 2:
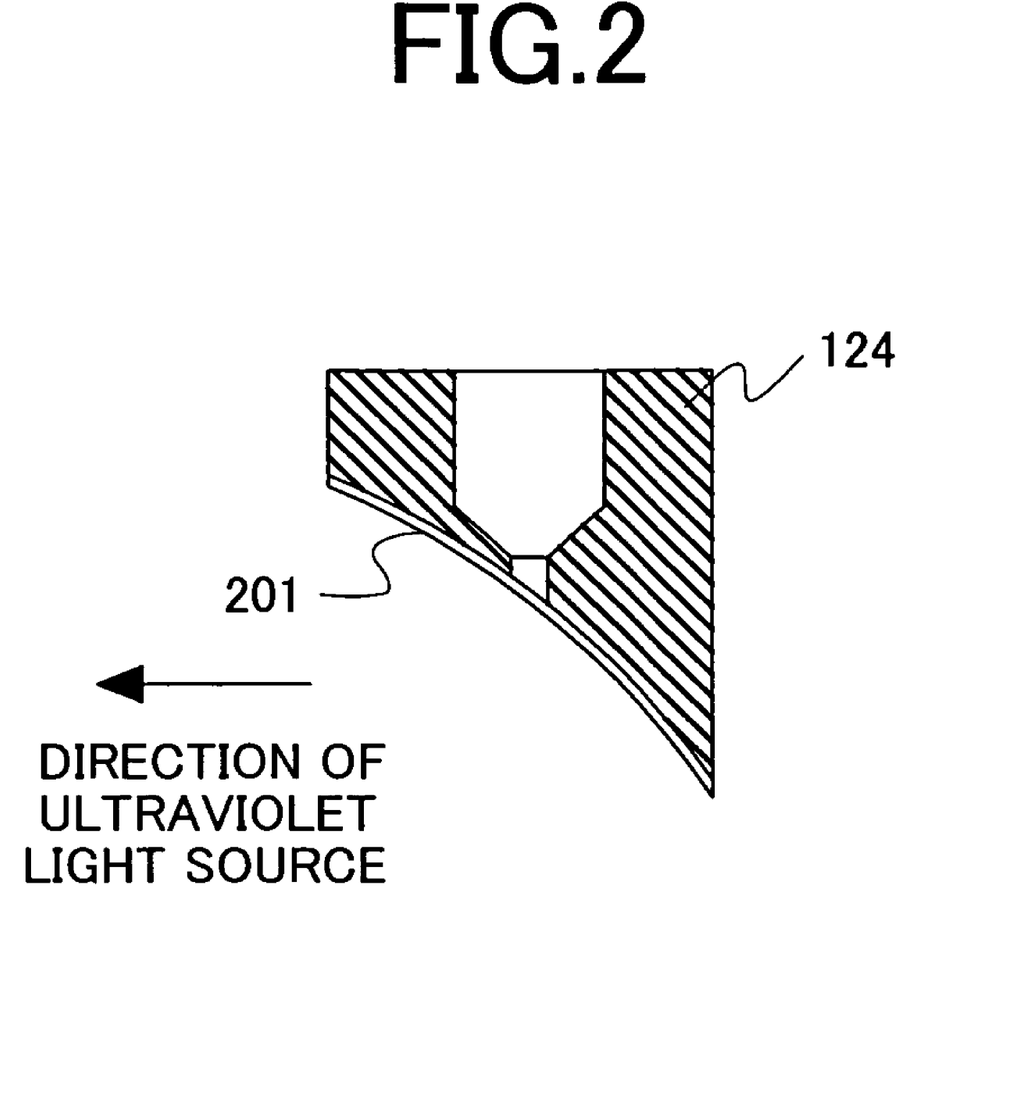
FIG. 2 is an explanatory diagram showing an example of the construction of an ultraviolet reflecting mirror.

FIG. 2 shows an example of the construction of the reflecting mirror. FIG. 2 shows a cross section containing the optical axis of the electron optical system and the optical axis of an ultraviolet optical system. The reflecting mirror 124 has a reflecting surface 201 of an aspheric shape such as a quadratic surface, a toroidal surface, or a combination thereof so that the reflecting mirror can reduce an image of the pinhole 123 and project the image on the sample surface. A nonmagnetic conducting material such as phosphor bronze is selected for fear the trajectory of an electron beam may be affected. The reflecting surface 201 is coated with aluminum (Al) exhibiting a reflectance with respect to ultraviolet rays. The inner diameter of a hole (opening) which penetrates through the reflecting mirror 124 and through which an electron beam passes is made as small as possible in the reflecting surface 201 and made large in the other part of the reflecting mirror in order to avoid contamination from an electron beam.

Figure 3A:
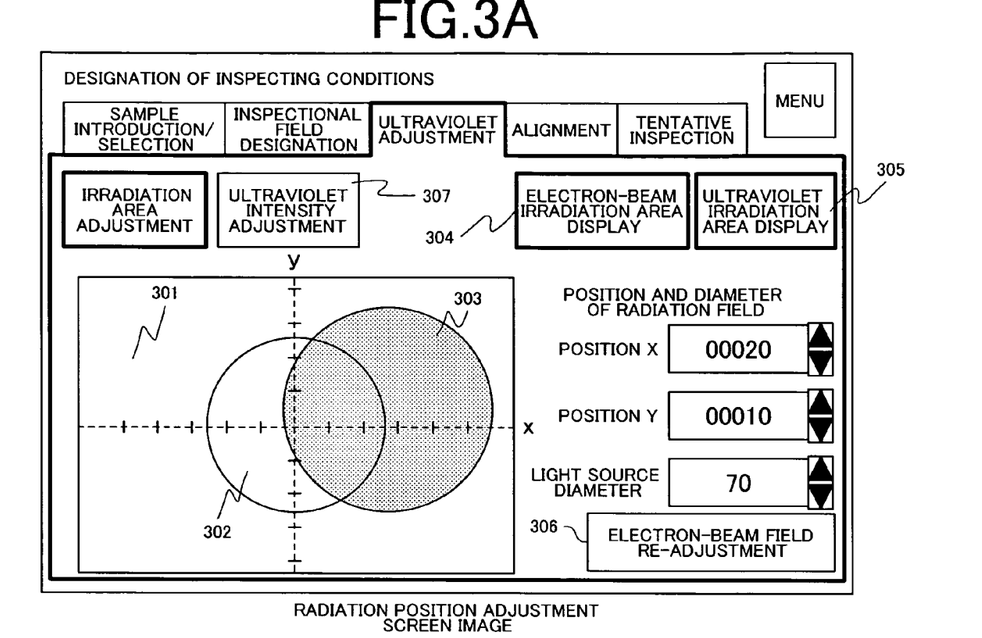
FIG. 3A and FIG. 3B show examples of monitor displays presenting progresses of an operation of limiting an ultraviolet irradiation area in an electron-beam irradiation area.
Figure 3B:
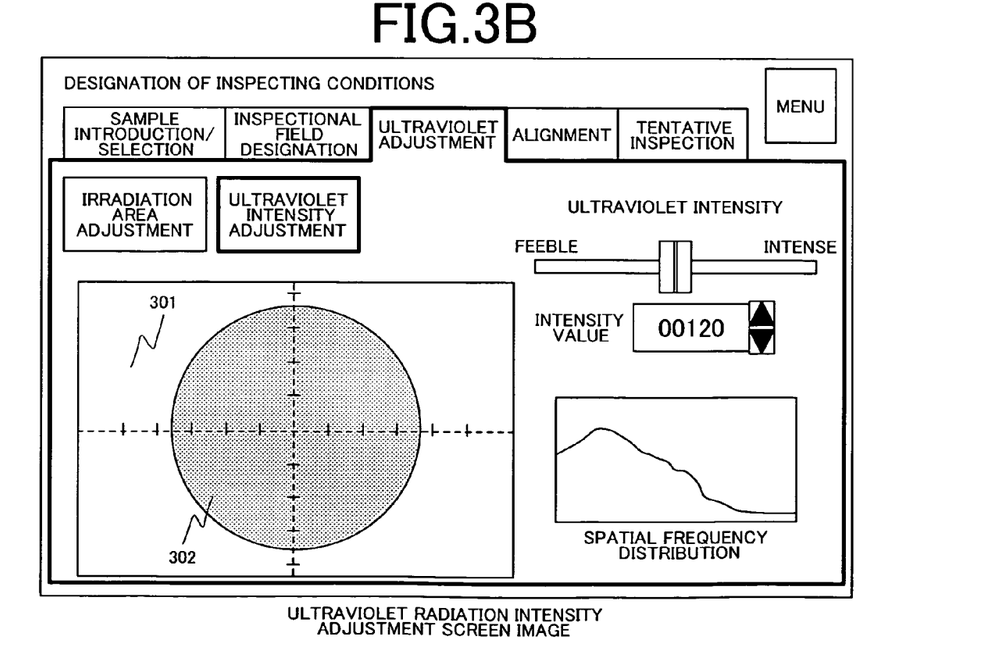

Next, a method of adjusting the irradiating conditions for ultraviolet rays employed in the present invention will be described below. FIGS. 3A and 3B show examples of display screen images on the monitor-inclusive input/output device 118 for adjustment of ultraviolet irradiation. FIG. 3A shows a screen image for use in performing an operation of limiting an ultraviolet irradiation area in an electron-beam irradiation area (hereinafter a limiting operation). FIG. 3B shows a screen image for use in adjusting the intensity of ultraviolet rays (hereinafter, intensity adjustment).

In a display area 301 in FIG. 3A, an electron-beam irradiation area and an ultraviolet irradiation area are displayed. For performing the adjusting operation, in order to eliminate the adverse effect of a distortion of an image caused by charging, a conductive adjustment sample is employed, or an adjustment conductor which is mounted in the sample stage 108 as described later and which has the same surface height as the sample surface is employed. When the screen image shown in FIG. 3A is invoked because a user has selected the squaring operation or the inspection apparatus control unit 117 decides at the time of starting an inspection system that the adjusting operation is needed, a dialog prompting the user to replace the sample with the adjustment sample is displayed, or the adjustment sample mounted on the sample stage 108 is moved so that it will come immediately below the objective lens 107. Otherwise, the user may be allowed to select either of the display of the dialog and the movement of the sample stage.

When an Electron-beam Irradiation area Display button 304 is pressed, the inspection apparatus control unit 117 operates the electron optical system control device 113, sets the electron optical system to the reflected-electron imaging mode, acquires a reflected-electron image, and displays the reflected-electron image (or the contour thereof) in the display area 301. The field occupied by the reflected-electron image is defined as an electron-beam irradiation area 302. At this time, as the operating mode of the optical image detector 112b, a normal imaging mode in which an image of a still object is fetched is selected.

If electron optical conditions have already been adjusted, the electron-beam irradiation area 302 is displayed in the center of the display area shown in FIG. 3A. When the electron-beam irradiation area 302 does not appear in the center of the display area 301, an electron optical adjustment screen image (not shown) is restored. The electron-beam irradiation area 302 is adjusted via the electron optical system control device 113 so that it will be displayed in the center. Even when the Electro-beam Irradiation area Display button 304 is re-pressed in order to cease irradiation of an electron beam to a sample, the electron-beam irradiation area 302 remains intact in the screen image or only the contour of the field is displayed.

When an Ultraviolet Irradiation area Display button 305 is pressed, the inspection apparatus control unit 117 ceases irradiation of an electron beam to a sample by driving a valve or blanker (neither shown) mounted in the middle of the electron optical system, and changes the operating mode of the electron optical system into an imaging mode in which photoelectrons generated with ultraviolet rays are imaged. The electron optical conditions to be satisfied at this time are stored in advance in the electron optical system control device 113. The electron optical conditions for each of reflected-electron imaging and photoelectron imaging are adjusted in advance so that images of the same magnification will be displayed.

Thereafter, the ultraviolet irradiation control device 125 increases an ultraviolet intensity via the ultraviolet light source 121 and ultraviolet transportation system 122 so that a photoelectron image of satisfactory brightness will be obtained because the intensity of ultraviolet rays irradiated to a sample is sufficient. An image of photoelectrons generated from a sample to which ultraviolet rays of a sufficient intensity are irradiated is, like a reflected-electron image, acquired by the image detection unit 112, and the photoelectron image 303 (or its contour) is displayed in the display area 301. Since the electron-beam irradiation area 302 and photoelectron image 303 are acquired under the optical conditions designated in order to keep a power constant, if the electron-beam irradiation area and photoelectron image are superposed on each other, an electron beam and ultraviolet rays can be irradiated to the same field.

In order to square the photoelectron image 303 with the electron-beam irradiation area 302, the pinhole 123 is moved on a plane perpendicular to the ultraviolet ray axis so that the centers thereof will be squared with each other. In the present embodiment, if a value is entered in each of Position X and Position Y spaces in FIG. 3A, or if a triangle mark is clicked, the drive shaft of the pinhole 123 is interlocked with the photoelectron image via the ultraviolet irradiation control device, and the photoelectron image 303 is moved within the display area 301. Otherwise, the center in brightness of the photoelectron image may be calculated, and the photoelectron image may be adjusted with the electron-beam irradiation area by calculating a magnitude of movement made by the pinhole 123 in terms of the coordinates representing the center.

Thereafter, the size of the pinhole is modified so that the area of the photoelectron image 303 will be limited in that of the electron-beam irradiation area 302. In the present embodiment, if a value is entered in the light source diameter space in FIG. 3A, or if a triangle mark is clicked, the size of the pinhole 123 is varied via the ultraviolet irradiation control device, and the size of the photoelectron image 303 is varied within the display area 301. When the photoelectron image cannot be limited in the electron-beam irradiation area by merely adjusting the size of the ultraviolet irradiation area, the electron optical system control device 113 is used to finely adjust the conditions for the condenser lens 102. Thus, the photoelectron image is limited in the electron-beam irradiation area. Since the size of the irradiation area is merely slightly modified, the sensitivity for inspection will not be adversely affected.

When an Electron-beam Area Readjustment button 306 is pressed, irradiation of ultraviolet rays is ceased while the contour of the photoelectron image 303 obtained by selecting a light source diameter closest to the diameter of the electron-beam irradiation area 301 is kept displayed on the screen. An electron beam is re-irradiated and a reflected-electron image is redisplayed in the display area 302. At the same time, a small window for electron optical system adjustment is displayed (not shown). While observing the display area 301, a user can adjust the size of the electron-beam irradiation area.

Through the foregoing operation, an ultraviolet irradiation area can be limited in an electron-beam irradiation area. Thereafter, the ultraviolet intensity is adjusted in order to balance negative charging, which occurs during reflection of electrons, with positive charging derived from generation of photoelectrons. When an Ultraviolet Intensity Adjustment button 307 in FIG. 3A is pressed, a transition is made to an ultraviolet intensity adjustment screen image shown in FIG. 3B. In ultraviolet intensity adjustment, the conductive sample employed in adjustment of an ultraviolet irradiation area cannot be used because charging does not occur. When this screen image is invoked, a dialog prompting a user to select employment of an adjustment insulator sample, which is mounted in another place on the sample stage 108 for the purpose of this adjustment, or introduction of a new insulator sample to the inspection apparatus is displayed. The user selects the ultraviolet intensity adjustment sample according to the situation of a sample to be inspected.

When the ultraviolet intensity adjustment screen image shown in FIG. 3B is selected, a reflected-electron image of the adjustment insulator sample is first obtained. The electron optical system control device 113 sets the electron optical conditions to reflected-electron imaging conditions, and displays a reflected-electron image detected by the image detection unit 112 in the display area 301. At this time, the surface of the adjustment sample is negatively charged due to electrons having the slightly high energy and being contained in an electron beam.

Thereafter, the user slides an adjustment bar indicated with Ultraviolet Intensity in FIG. 3B, or enters an intensity value in an intensity entry space. Thus, ultraviolet rays are irradiated with the intensity thereof gradually increased. The ultraviolet irradiation control device 125 irradiates ultraviolet rays according to the entry, controls the ultraviolet transportation system 122, and thus adjusts the ultraviolet intensity. During the irradiation of ultraviolet rays, the reflecting plane for reflected electrons that has receded from the sample surface due to negative charging approaches the sample surface along with an increase in the ultraviolet intensity. Therefore, the sample surface is gradually clearly observed with a high resolution. When a reflected-electron image of a desired contrast is obtained, increasing the ultraviolet intensity is ceased and the ultraviolet intensity is determined. In the present embodiment, a spectrum of spatial frequencies obtained by Fourier-transforming image data is displayed in the screen image shown in FIG. 3B in order to quantitatively grasp the quality of the reflected-electron image. While observing the spectrum, the user should merely adjust the ultraviolet intensity so as to increase a spectral intensity of a high-frequency component as much as possible, and can therefore easily find an optimal ultraviolet intensity.

Figure 4:
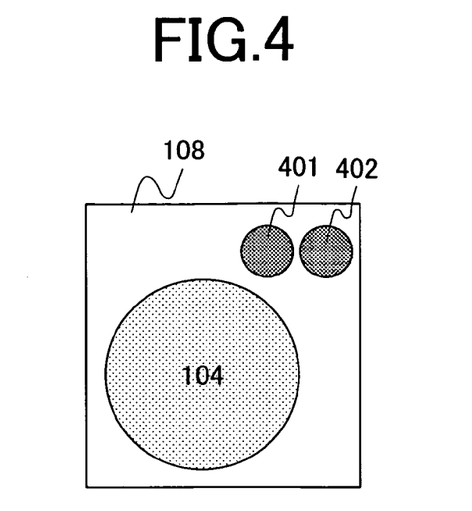
FIG. 4 shows an example of a sample stage in accordance with the present invention.

FIG. 4 shows an example of the positions of adjustment samples mounted on the sample stage 108. In FIG. 4, the sample stage 108 is seen from the objective lens side. The sample 104 such as a wafer is mounted on the sample stage 108. A conductive adjustment sample 401 for the limiting operation and an ultraviolet intensity adjustment sample 402 are mounted on part of the stage that does not hinder the inspection of the sample 104. The samples are mounted so that the sample surfaces will have the same height as the surface of the sample 104. The edges of samples are far from the center of a field of view by at least substantially 5 mm so that the equipotential surface on the surface of the stage will be parallel with the sample surfaces.

The conductive adjustment sample 401 is, for example, a silicon (Si) wafer or has a metallic film formed on the Si wafer, and is mounted so that the surface thereof will be electrically connected to the sample stage 108. An insulating film serving as the ultraviolet intensity adjustment sample 402 is, for example, an oxide film formed on the Si wafer. Even when an irradiation current value remains unchanged, since the magnitude of negative charging occurring during reflection of electrons varies depending on the dielectric constant of the insulating film, a material and a film thickness that are as close as possible to those of the sample to be inspected are adopted. When multiple kinds of insulating films are used in a sample to be inspected, the film thickness of the sample varies, or the dielectric constant thereof varies depending on a film formation process, since adjustment cannot be performed using the same insulating film, multiple kinds of the ultraviolet intensity adjustment insulating-film samples 402 may be prepared. Otherwise, the adjustment sample may be used to perform rough adjustment, and fine adjustment may be performed during production of an inspection recipe.

Through the foregoing adjustment, an electron-beam irradiation area and an ultraviolet irradiation area are spatially adjusted with each other, and an ultraviolet intensity suitable for cancellation of negative charging during reflection of an electron beam is determined. An inspecting operation for inspecting a sample to be inspected is then initiated.

Figure 5:
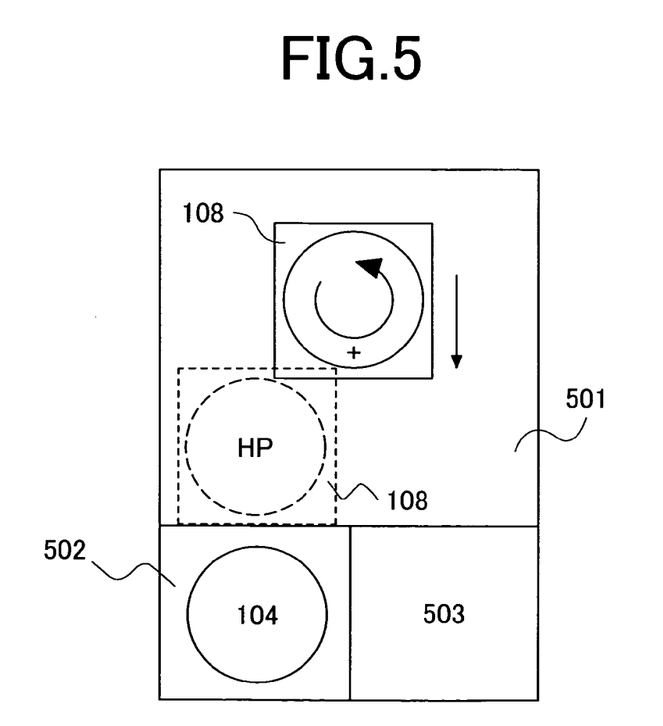
FIG. 5 is a top view for explaining the fundamental configuration of an inspection apparatus of the present invention.

An inspection procedure will be described below in conjunction with FIG. 5 that is a schematic top view of an inspection apparatus in accordance with the present invention, and FIG. 6 that is an inspection flowchart. FIG. 5 shows a sample chamber 501, a load lock chamber 502, and a charging cancellation chamber 503. A vacuum pump, a power supply rack, and other devices that are not referred to during a description to be made below are not shown.

Figure 6:
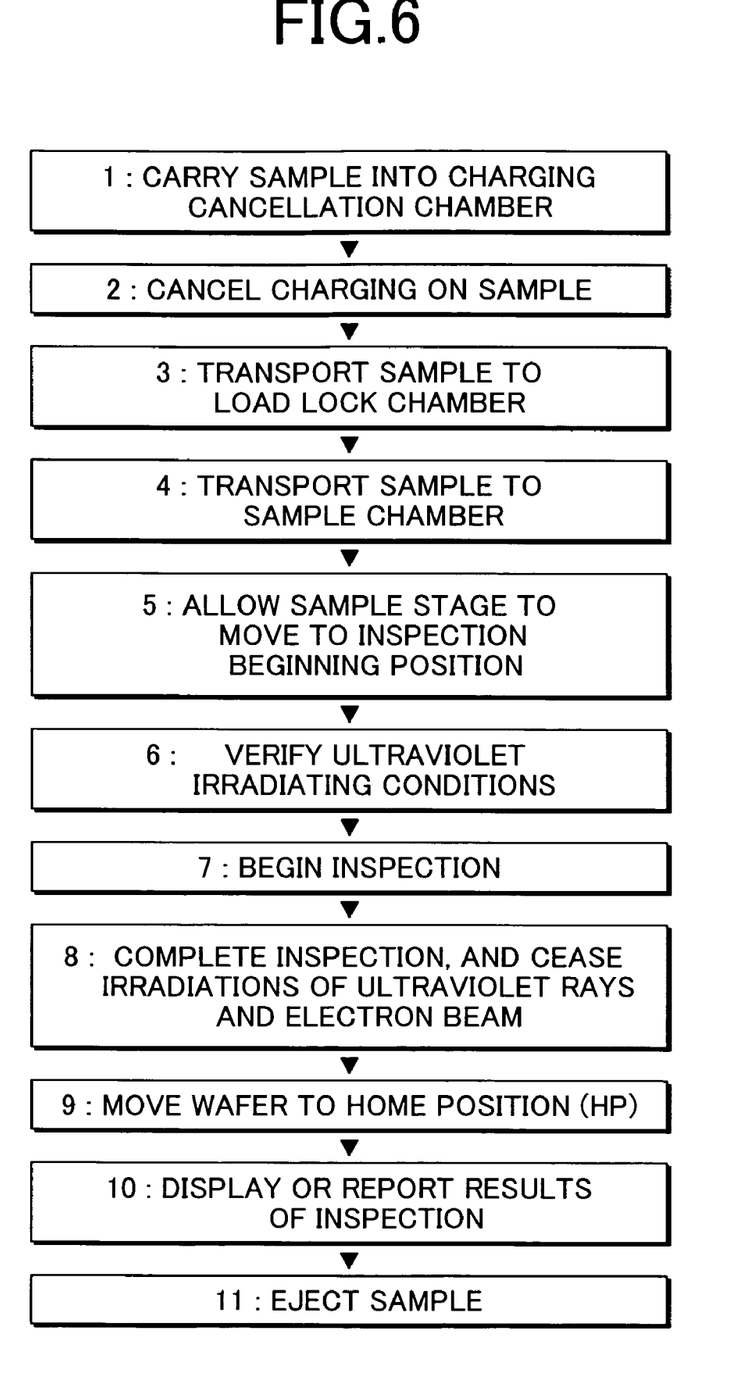
FIG. 6 is a flowchart describing an inspection procedure in accordance with the present invention.

To begin with, a wafer, a disk medium, or any other sample to be inspected is introduced to the charging cancellation chamber 503, and has charging, which has already occurred on the sample, canceled (steps 1 and 2 in the flowchart of FIG. 6).

Charging considered therein is not charging which develops about several volts, which occurs during reflection of electrons, and whose cancellation is an object of the present invention, but is inhomogeneous charging which may develop about 100 V and is derived from other processing of a film formation process or an etching process. When such significant charging is left intact, electron reflecting conditions cannot be adjusted at all. The surface of a sample to be inspected is homogenized to have a predetermined potential applied thereon (in many cases, a ground potential). As a method of canceling charging or making a potential uniform as a whole, for example, there is ultraviolet irradiation to the whole sample surface or electron-beam irradiation thereto. FIG. 5 shows a case where charging is canceled by irradiating ultraviolet rays to the whole sample surface in the charging cancellation chamber. In this case, a sample is held in the atmosphere. The sample is not carried to the load lock chamber 502 until charging cancellation work is completed. When electron-beam irradiation is adopted as the charging cancellation method instead of ultraviolet irradiation, the charging cancellation chamber 503 has to be kept in a vacuum. The sample is first carried to the load lock chamber 502, and then carried to the charging cancellation chamber 503 in which the vacuum is sustained. However, when charging of the sample is canceled in advance, the charging cancellation chamber 503 may be excluded.

After charging of an entire sample is canceled in the charging cancellation chamber 503, the sample is carried to the load lock chamber 502, and the load lock chamber is evacuated (step 3 in the flowchart of FIG. 6).

When the vacuum level becomes almost identical to the pressure in the sample chamber 501, the sample is carried to the sample chamber 501 (step 4 in the flowchart of FIG. 6).

In the sample chamber 501, the sample stage 108 has been moved to a sample carried position (hereinafter a home position HP). When the sample 104 is moved from the load lock chamber 502 to the sample chamber 501, the sample chamber 501 and load lock chamber 502 are separated from each other by handling a gate valve or the like.

In the present embodiment, the sample stage 108 is moved in one direction (the direction of an arrow drawn with a straight line in FIG. 5) while the sample is being rotated. The entire surface of the sample is thus inspected. The sample is inspected from the periphery thereof to the center thereof. The movements may be orthogonal two dimensional motions (x-y motion) in the case of a wafer pattern inspection. When the sample stage 108 receives the sample at the HP, the sample stage is moved to an inspection beginning position (step 5 in the flowchart of FIG. 6).

The sample stage is rotated, and ultraviolet rays and an electron beam are irradiated under conditions adjusted in advance. A reflected-electron image is then acquired. At this time, a TDI mode is selected so that the image detection unit 112 can be interlocked with the movement of the sample and an image can be acquired without the necessity of stopping the sample. Image assessment is performed in order to decide whether the ultraviolet irradiating conditions fall within a permissible range and a reflected-electron image is satisfactory. An amount of ultraviolet rays and the position of the sample are readjusted (step 6 in the flowchart of FIG. 6).

After the ultraviolet irradiating conditions are finely adjusted, an inspecting operation is initiated (step 7 in the flowchart of FIG. 6).

A reflected-electron image acquired during inspection is checked by the defect decision block 116*b* in order to make a decision on the presence or absence of a foreign matter. Coordinates representing the position of the sample attained when a foreign matter is detected are stored successively. When inspection of the entire sample or a user-designated inspecting range is completed, irradiations of an electron beam and ultraviolet rays are ceased (step 8 in the flowchart of FIG. 6). The sample is moved to the HP (step 9 in the flowchart of FIG. 6).

Ceasing irradiations of an electron beam and ultraviolet rays are not achieved by stopping the electron-beam source and ultraviolet light source but achieved by intercepting the electron beam and ultraviolet rays with insertion of shields. This is intended to sustain stable irradiations of the electron beam and ultraviolet rays. The inspection apparatus displays the results of defect inspection or transmits the results of defect inspection to a server that manages line production (not shown) (step 10 in the flowchart of FIG. 6).

If re-inspection is not needed, the sample is ejected (step 11 in the flowchart of FIG. 6), and an inspecting operation is initiated for the next sample.

As mentioned above, according to the present embodiment, even when a sample to be inspected is an insulating-film wafer, detecting sensitivity will not be degraded by the adverse effect of negative charging occurring during reflection of electrons, but stable inspection can be executed.

Embodiment 2

In the present embodiment, modulation of the intensity of ultraviolet rays by the ultraviolet transportation system 122 shown in FIG. 1 is achieved merely by inserting a filter. In the present embodiment, the ultraviolet light source 121 is a light source capable of feeding a sufficient amount of ultraviolet rays for the purpose of acquiring a photoelectron image.

Figure 7:
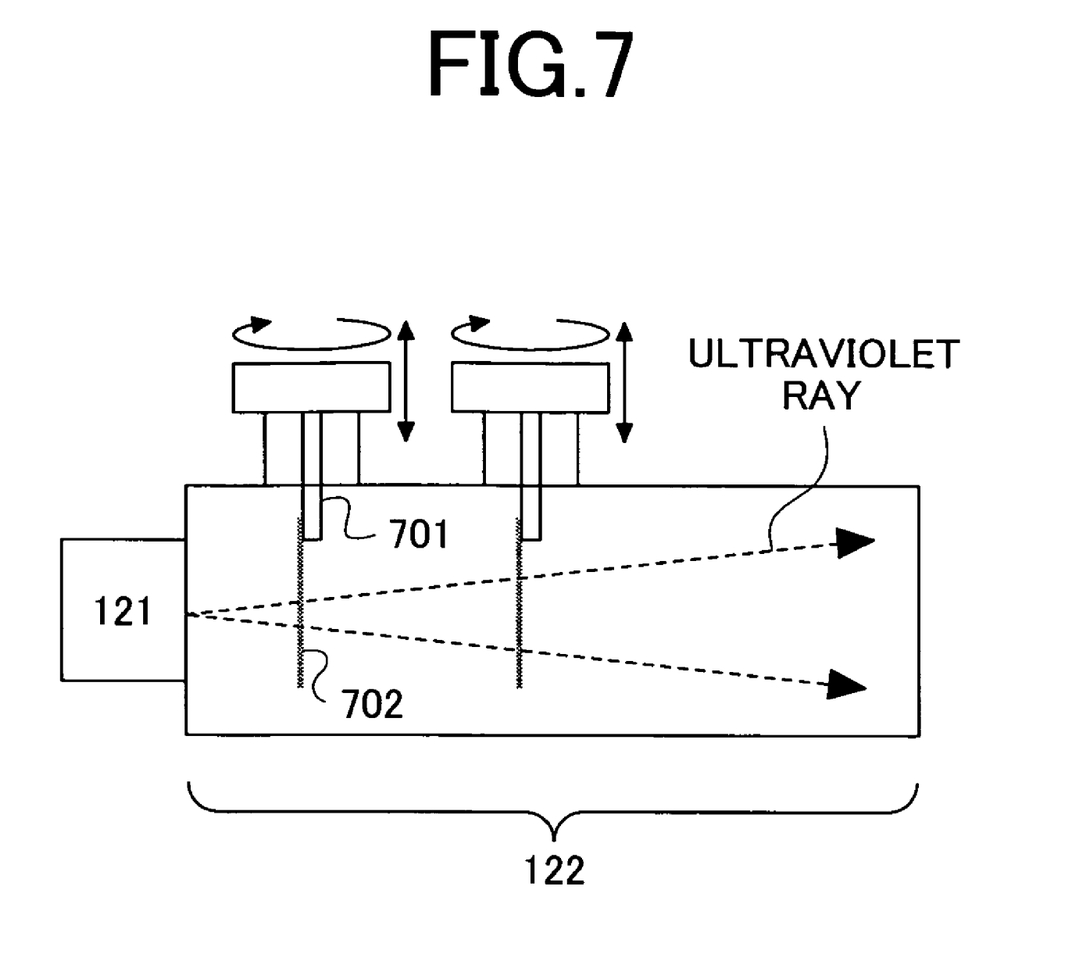
FIG. 7 is an explanatory diagram showing another example of the construction of an irradiated ultraviolet intensity adjustment device employed in an embodiment 2 of the present invention.

In the ultraviolet transportation system 122 shown in FIG. 7, a filter 702 exhibiting a finite transmittance with respect to ultraviolet rays is attached to a rod 701 that can perform plunging and rising motions relative to the ultraviolet ray axis and perform rotating motion with the axis thereof as a center. Multiple filters 702 (two filters in FIG. 7) may be included. The filter 702 may have a filtering material attached to an appropriate holding structure.

When a photoelectron image is acquired, the filters 702 are withdrawn from the ultraviolet ray path by a moving mechanism. A maximum amount of light is therefore provided. When an amount of ultraviolet rays is adjusted, the filters 702 are inserted into the light path. In order to finely adjust the amount of ultraviolet rays, the filters 702 are rotated about the axes of the respective rods 701. When the filters 702 are rotated, an effective distance by which ultraviolet rays propagate to pass through each of the filters gets longer. Consequently, the transmittance can be successively decreased.

According to the present embodiment, an amount of ultraviolet rays can be adjusted using a simple structure.

Embodiment 3

In the aforesaid embodiments, an operation of limiting an ultraviolet irradiation area in an electron-beam irradiation area is performed mainly by handling the pinhole on the ultraviolet ray path. However, in the present embodiment, a diaphragm for limiting a field of view is mounted on the light path of an electron beam in order to improve the precision in limiting the ultraviolet irradiation area in the electron-beam irradiation area.

Figure 8:
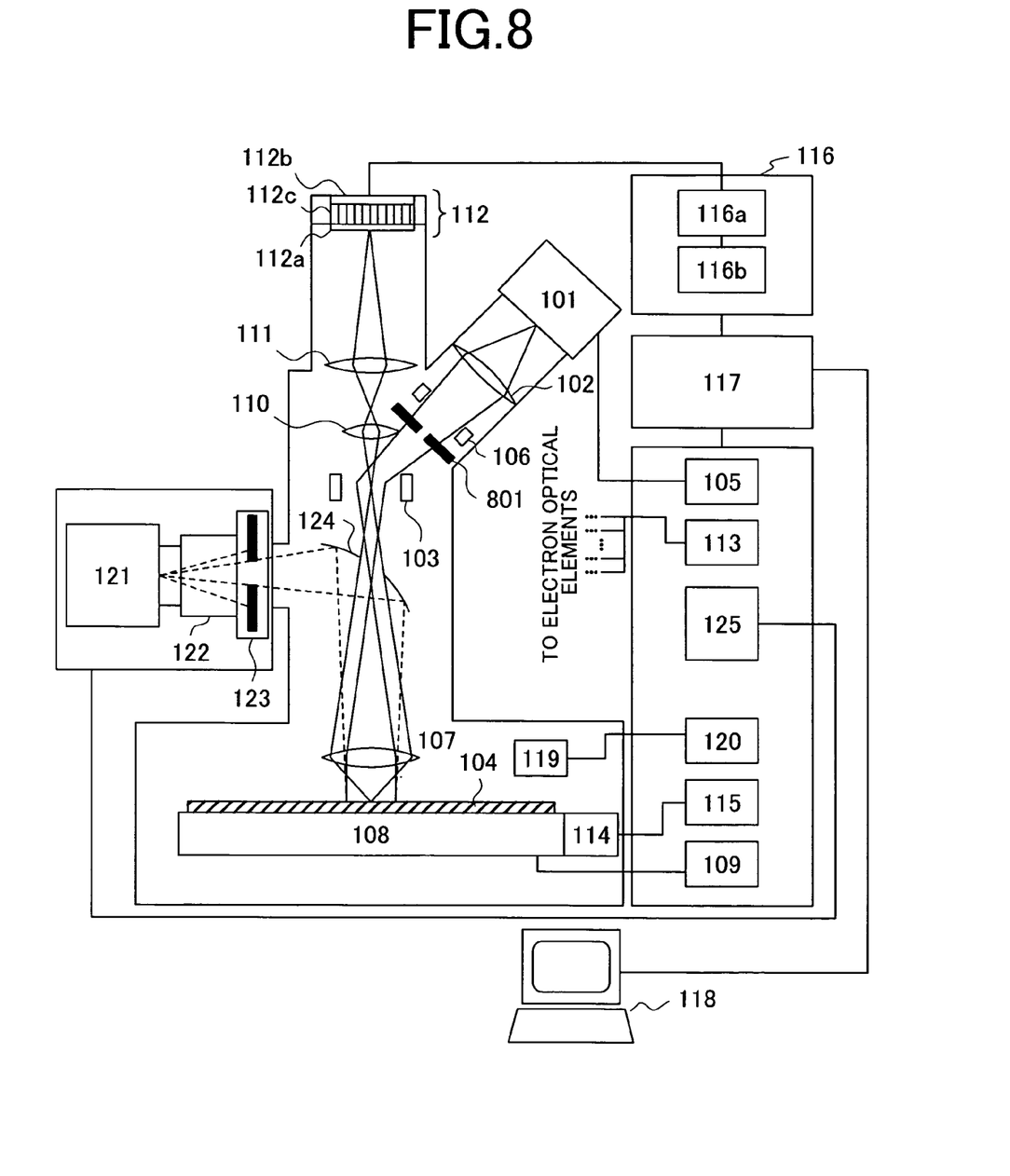
FIG. 8 is an explanatory diagram showing an example of a configuration of an embodiment 3 of the present invention in which a diaphragm is mounted on the optical path of an electron optical system.

FIG. 8 shows the configuration of an electron beam inspection apparatus having a diaphragm 801 mounted on the optical path of the electron optical system. In FIG. 8, the same reference numerals are assigned to components identical to those shown in FIG. 1. The description of the components will be omitted. The diaphragm 801 is mounted in an irradiation optical system for fear the presence of the diaphragm may adversely affect an imaging optical system. In the present configuration, the shape and size of an electron-beam irradiation area are determined by the diaphragm 801. When the shape of the pinhole 123 is designed in line with the shape of the diaphragm 801, the shapes and sizes of an ultraviolet irradiation area can be included by an electron-beam irradiation area.

Figure 9:
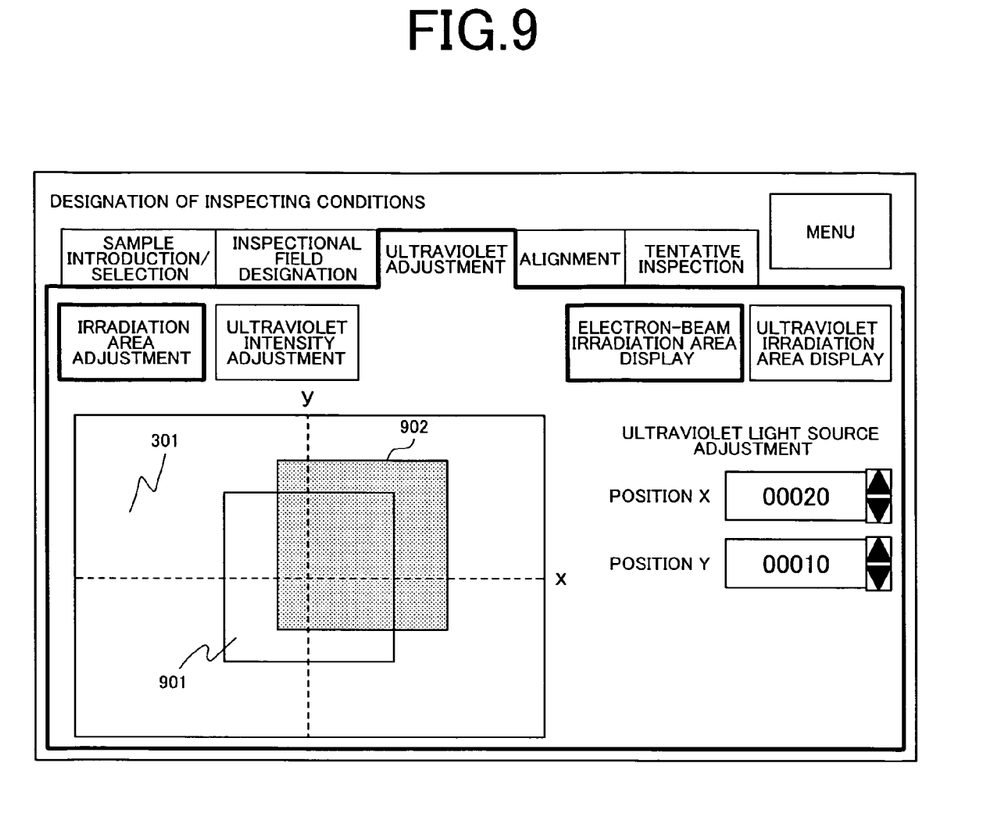
FIG. 9 shows an example of a monitor display presenting a progress of an operation of limiting an ultraviolet irradiation area in an electron-beam irradiation area according to the embodiment 3.

FIG. 9 shows an example of a monitor display attained during a adjusting operation according to the present embodiment. An electron-beam irradiation area 901 is shown in the display area 301 on the monitor. In this example, the shape of the diaphragm 801 is supposed to be adjusted. The electron-beam irradiation area 901 shown therein need not be an irradiated area of an actual electron beam, but may be an equivalent irradiation area deduced from the shape of the diaphragm 801. When ultraviolet rays are introduced and a photoelectron image 902 is displayed, the positional relationship between an electron-beam irradiation area and an ultraviolet irradiation area is specified. The position of the pinhole 123 determining the ultraviolet irradiation area is shifted so that both the fields will be squared with each other. The limiting operation is then completed.

According to the present embodiment, an ultraviolet irradiation area can be limited in an electron-beam irradiation area by adjusting a irradiation position without the necessity of adjusting the size of the ultraviolet irradiation area.

Embodiment 4

In the aforesaid embodiments, a sample for ultraviolet adjustment is supposed to be a flat surface sample without any pattern. In the present embodiment, an adjustment sample making it easy to adjust the ultraviolet irradiating conditions will be introduced.

Figure 10A:
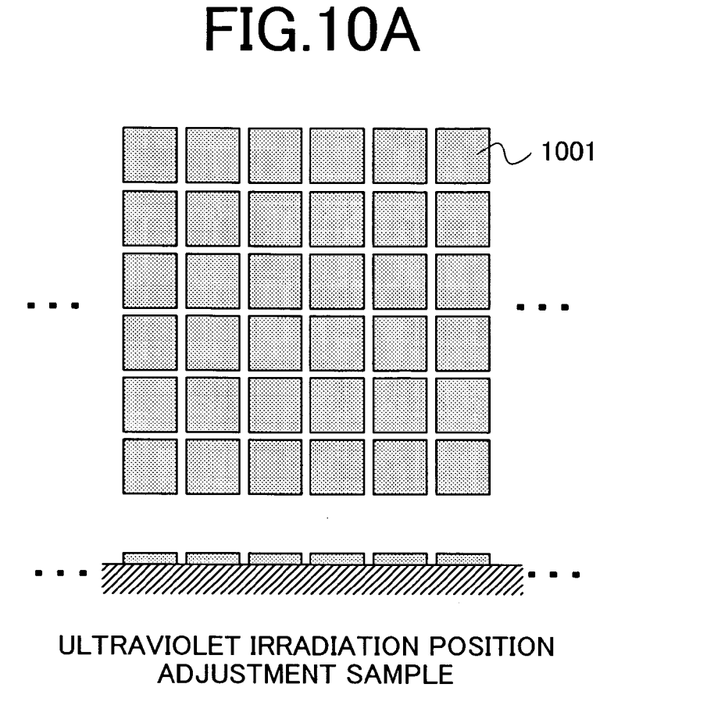
FIG. 10A and FIG. 10B are explanatory diagrams showing examples of adjustment samples employed in an embodiment 4 of the present invention.

FIG. 10A shows an ultraviolet radiation position adjustment sample. The sample has an array of rectangular patterns 1001 formed on a conductive substrate using a conductive material whose photoelectron emission efficiency is different from that of the material of the substrate. Moreover, the rectangular patterns have a thickness of about 200 microns with respect to the substrate surface. When a reflected-electron image is acquired, since the irregularities of the rectangular pattern array are reflected on the image, the rectangular pattern array can be observed. On the other hand, when ultraviolet rays are irradiated in order to acquire a photoelectron image, a contrast is produced due to a difference between materials. Consequently, the rectangular pattern array can be observed.

The array of rectangles is used as scales providing coordinates, whereby a user can grasp to which area on a sample an electron beam or ultraviolet rays are irradiated. At this time, the user need not strictly calibrate an optical system and need not be concerned about a variation in the conditions for the optical system.

Figure 10B:
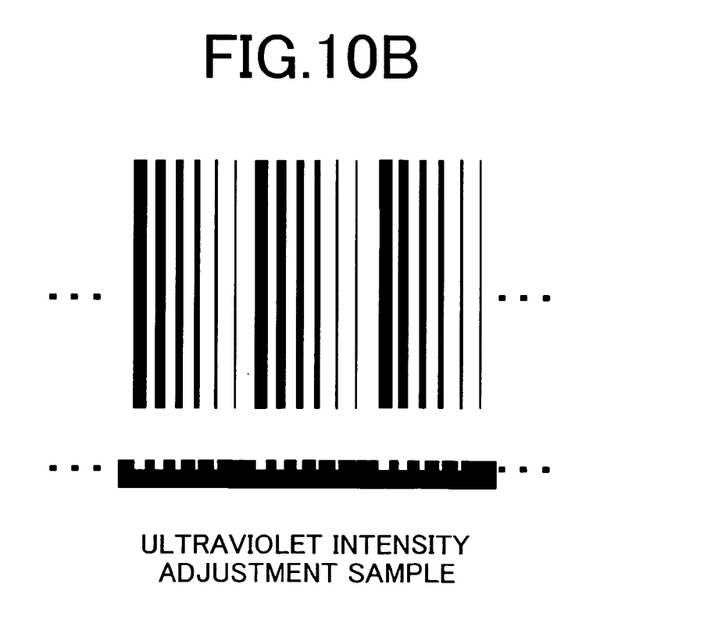

FIG. 10B shows an example of an ultraviolet intensity adjustment sample. The sample has grooves of different widths formed in an insulating film. As illustrated, a set of grooves ranging from the thickest groove to the thinning groove is repeated to form an array of sets of grooves. When this sample is employed, if the sample is negatively charged and a reflecting plane for electrons recedes from the sample surface, the sensitivity to the shape of the surface is degraded. Consequently, the lines of only the thick grooves can be observed. When ultraviolet rays are irradiated to the sample surface in order to cancel negative charging, as the reflecting plane for electrons approaches the sample surface, the thinner grooves can be observed. A user should merely continue the irradiation of ultraviolet rays until the grooves of a desired width can be observed. Aside from the grooves, similar convex linear patterns may be formed on the sample surface. Moreover, the widths of grooves or lines may not be varied but the widths thereof may be set to the same value but the depths thereof or heights thereof may be varied in order to form patterns. Nevertheless, the same adjustment can be performed.

Using the present embodiment, an ultraviolet irradiation area and an electron-beam irradiation area can be easily squared with each other, and an ultraviolet intensity can be optimally adjusted.

The embodiments to which the present invention is applied have been described so far. The present invention encompasses a combination of any of the embodiments 1 to 4.

According to the present invention, positive charging derived from ultraviolet irradiation and negative charging occurring during imaging of reflected electrons can be highly precisely balanced. Negative charging derived from electron-beam irradiation can be canceled even from a sample made of an insulating material. An ultramicroscopic foreign matter or defect can be highly sensitively detected at a high speed.

What is claimed is:

1. An electron beam inspection apparatus including:
   an electron optical system that irradiates a planar electron beam, which is emitted from an electron source, to irradiate a range covering a field of view on a sample;
   means for applying a voltage to the sample;
   electron beam imaging means for converging electrons, which are reflected from the sample due to the irradiated planar electron beam, so as to acquire a reflected-electron image;
   means that has the sample mounted thereon and moves the sample with respect to the irradiated planar electron beam;
   means that uses the reflected-electron image to extract a foreign matter or defect on the sample, and records a position of the foreign matter or defect on an image thereof; and
   an ultraviolet irradiation system that irradiates ultraviolet rays to irradiate an area of the sample concurrently with the electron optical system irradiating the planar electron beam to irradiate the range, comprising:
   means for adjusting so that the range irradiated by the planar electron beam includes area concurrently irradiated by the ultraviolet rays; and
   means for adjusting an intensity of the ultraviolet rays irradiated within the irradiated range of the concurrently-irradiated planar electron beam while sustaining imaging conditions for the reflected-electron image.

2. The electron beam inspection apparatus according to claim 1, comprising means that uses the electron-beam imaging means to converge photoelectrons, which are generated from the sample due to the irradiation of the ultraviolet rays, so as to acquire a photoelectron image, and displays the irradiated area of the ultraviolet rays.

3. The electron beam inspection apparatus according to claim 2, comprising means that adjusts the position and size of the irradiated area of the ultraviolet rays so that the contour of the photoelectron image will be limited in the contour of the reflected-electron image.

4. The electron beam inspection apparatus according to claim 1, wherein negative charging in the range irradiated by the planar electron beam derived from the irradiated planar electron beam is neutralized.

5. The electron beam inspection apparatus according to claim 1, wherein the ultraviolet irradiation system includes an ultraviolet light source and a reflecting surface that changes the advancing direction of the ultraviolet rays from one to another so as to irradiate the ultraviolet rays to the sample.

6. The electron beam inspection apparatus according to claim 5, wherein the reflecting surface is located in the middle of the electron optical system, and has an opening through which the electron beam passes and which is intended to align the direction in which the electron beam is irradiated to the sample with the direction in which the ultraviolet rays are irradiated to the sample.

7. The electron beam inspection apparatus according to claim 5, wherein the ultraviolet irradiation system has means, which adjusts an amount of the ultraviolet rays, and a pinhole interposed between the ultraviolet light source and the reflecting surface.

8. The electron beam inspection apparatus according to claim 7, wherein a diaphragm for limiting the field of view on the sample is mounted on an optical path of the electron optical system, and the diaphragm and pinhole are used to limit a shape and size of the area irradiated by the ultraviolet rays to within a shape and size of the range concurrently irradiated the planar electron beam.

9. An electron beam inspection apparatus including:

an electron optical system that shapes an electron beam, which is emitted from an electron source, into a planar electron beam, and irradiates the planar electron beam to irradiate a range covering a field of view on a sample;

means for applying a negative voltage to the sample;

an electron-beam imaging means that converges electrons, which are reflected from the sample due to the irradiated planar electron beam, so as to acquire a reflected-electron image;

means that has the sample mounted thereon and moves the sample with respect to the irradiated planar electron beam;

means that uses the reflected-electron image to extract a foreign matter or defect on the sample, and records a position of the foreign matter or defect on an image thereof; and an ultraviolet irradiation system that irradiates ultraviolet rays to irradiate an area of the sample concurrently with the electron optical system irradiating the planar electron beam to irradiate the range:

means for adjusting so that the range irradiated by the planar electron beam includes area concurrently irradiated by the ultraviolet rays; and means for adjusting an intensity of the ultraviolet rays irradiated within the irradiated range of the concurrently-irradiated planar electron beam while sustaining imaging conditions for the reflected-electron image, wherein negative charging in the range irradiated by the planar electron beam derived from the irradiated planar electron beam is neutralized.

10. An electron beam inspection method including:

a step of irradiating a planar electron beam to irradiate a range covering a field of view on a sample, to which a voltage is applied, through an electron optical system;

a step of converging electrons, which are reflected from the sample due to the irradiated planar electron beam, so as to acquire a reflected-electron image;

a step of extracting a foreign matter or defect on the sample using the reflected-electron image, and recording and displaying a position of the foreign matter or defect on an image thereof; and a step of alleviating negative charging on the sample, which is derived from the irradiated planar electron beam, by irradiating ultraviolet rays to irradiate an area of the sample concurrently with the electron optical system irradiating the planar electron beam to irradiate the range, comprising the steps of:

limiting the range irradiated by the planar electron beam to within the area concurrently irradiated by the ultraviolet rays; and adjusting an amount of the ultraviolet rays irradiated within the irradiated range of the concurrently-irradiated planar electron beam while sustaining imaging conditions for the reflected-electron image.

11. The electron beam inspection method according to claim 10, comprising a step of converging photoelectrons, which are generated from the sample due to the irradiation of the ultraviolet rays, so as to acquire a photoelectron image.

12. The electron beam inspection method according to claim 11, wherein the position and size of the irradiated area of the ultraviolet rays are adjusted so that the contour of the photoelectron image will be limited in the contour of the reflected-electron image.

13. The electron beam inspection method according to claim 12, wherein negative charging on the sample surface in the range irradiated by the planar electron beam derived from the irradiated planar electron beam is neutralized.

14. The electron beam inspection method according to claim 11, wherein negative charging on the sample surface in the range irradiated by the planar electron beam derived from the irradiated planar electron beam is neutralized.

15. The electron beam inspection method according to claim 10, wherein negative charging on the sample surface in the range irradiated by the planar electron beam derived from the irradiated planar electron beam is neutralized.

* * * * *